United States Patent
Koschmieder et al.

(10) Patent No.: US 6,252,696 B1
(45) Date of Patent: Jun. 26, 2001

(54) SUBASSEMBLY FOR GENERATING AN OPTICALLY ACTIVE SLIT

(75) Inventors: Ingo Koschmieder; Guenter Link, both of Jena; Dietmar Steinmetz, Bucha; Egon Luther, Cospeda, all of (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/522,546

(22) Filed: Mar. 10, 2000

(30) Foreign Application Priority Data

Mar. 12, 1999 (DE) ............................................... 199 10 942

(51) Int. Cl.$^7$ ..................................................... G02B 26/02
(52) U.S. Cl. ............................. 359/232; 359/227; 359/230
(58) Field of Search ..................................... 359/227, 230, 359/232, 233, 738; 396/452, 483, 484

(56) References Cited

U.S. PATENT DOCUMENTS

| | | | |
|---|---|---|---|
| 5,508,838 | * | 4/1996 | Shimizu et al. ...................... 359/232 |
| 5,661,589 | * | 8/1997 | Meyer ................................... 359/232 |

* cited by examiner

*Primary Examiner*—James Phan
(74) *Attorney, Agent, or Firm*—Reed Smith LLP

(57) ABSTRACT

A subassembly for generating an optically active slit with a changeable slit width s, preferably for slit lamps, with two slit jaws which are displaceable relative to one another at a straight-line guide and between which the slit is formed, wherein one of two guide paths is allocated to each slit jaw. In a subassembly for generating an optically active slit, the guide paths are formed at portions of a guide rail which project out freely in the displacement directions of the slit jaws from a clamping position which is fixed with respect to the frame. The guide rail can accordingly expand without hindrance in the displacement direction under the influence of temperature without the parallelism of the slit being affected thereby.

12 Claims, 2 Drawing Sheets

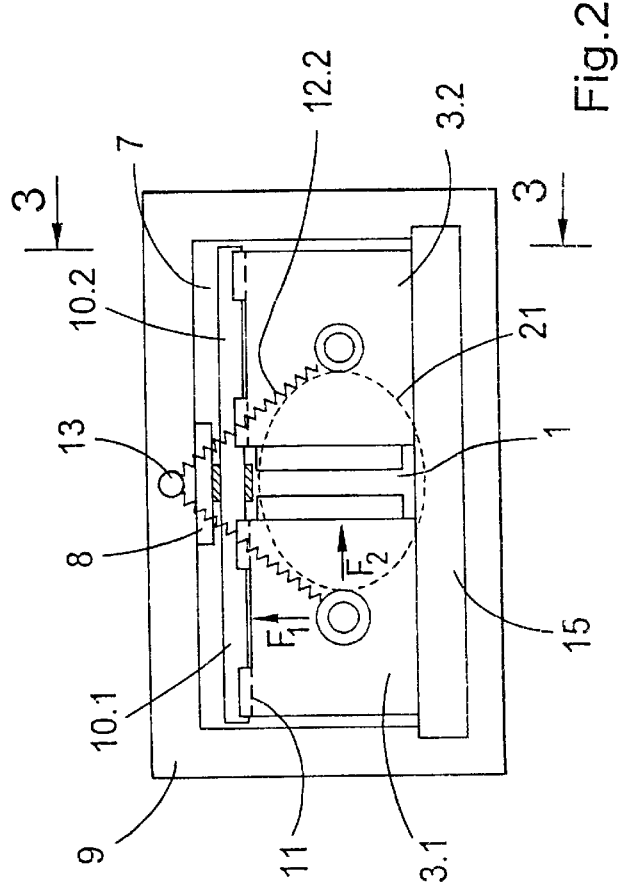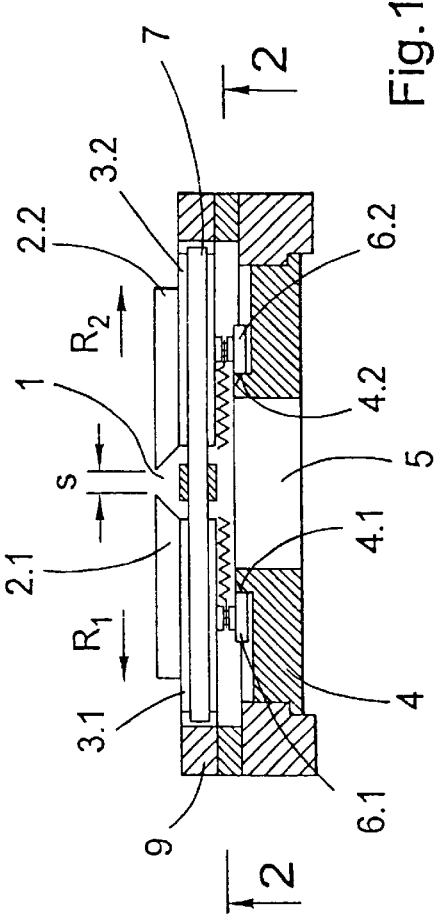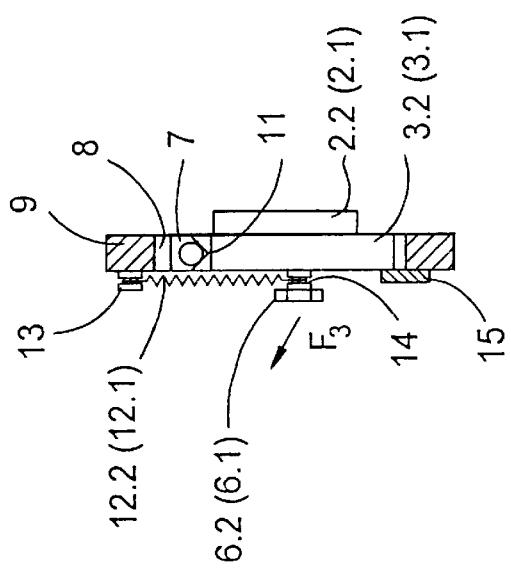

SUBASSEMBLY FOR GENERATING AN OPTICALLY ACTIVE SLIT

BACKGROUND OF THE INVENTION a) Field of the Invention

The invention is directed to a subassembly for generating an optically active slit with a changeable slit width s, preferably for slit lamps, with two slit plates or slit jaws which are displaceable relative to one another at a straight-line guide and between which the slit is formed, wherein one of two guide paths is allocated to each slit jaw.

b) Description of the Related Art

In optical instrument engineering, it is frequently necessary to generate illuminated fields of different geometric shapes with a virtually uniform illumination. One shape of illuminated field that is very frequently required is a light slit which is adjustable in width and length with an exactly parallel limiting of the slit width. Precision guidance of the slit-shaping structural component parts and a high edge quality at the slit jaws are needed to generate a light gap of this kind with high-contrast, sharp image borders.

A preferred application for subassemblies for generating an optically active slit is the slit lamp, which is frequently used for ophthalmologic diagnosis. It comprises essentially a stereo microscope and a projection device, both of which are arranged so as to be movable on a carrying system and coordinated with one another. The projection device makes it possible to generate geometrically different light fields. It is coupled with the stereo microscope in such a way that the center of the illumination field plane generally coincides with the center of the observation plane.

For example, a slit width which is adjustable from "zero" to 14 mm in a continuous and sensitive manner is required for applications of the kind mentioned above, wherein "zero" signifies an absolutely tight closing of the slit. The length of the slit can be between 0.3 mm and 14 mm, for example; further, the slit must often be swivelable by at least ±90° about the optical axis.

A significant problem in slit-forming optical subassemblies continues to be that the function-related caused proximity of the light housing which contains the illumination source giving off heat causes temperature fluctuations which disadvantageously affect the parallelism of the slit and which require a slit jaw guide that still generates a light slit satisfying requirements with respect to quality in spite of the influence of temperature.

The slit jaw guides known from the prior art have straight guide elements based on sliding friction or rolling friction in which two slit jaws which are displaceable relative to one another for changing the slit width are pretensioned against a guide path arranged at the frame by means of correspondingly constructed sliding or rolling guide elements so as to be free of play.

A disadvantage in all of the known technical solutions in this respect is the transmission of thermal and mechanical influences to the slit jaws which still occurs to an undesirably high degree and the consequent unwanted influence on the slit parallelism which manifests itself, for example, in the inability of the slit to close absolutely tight. To this extent, in spite of the large number of solutions that are already known, there is still a need for development, the aim of which is to reduce the troublesome influences and their consequences.

OBJECT AND SUMMARY OF THE INVENTION

Based on this prior art, it is the primary object of the invention to further develop a subassembly of the type mentioned above for generating an optically active slit in such a way that the consequences of external influences on the parallelism of the light slit are further reduced.

According to the invention, it is provided in a subassembly for generating an optically active slit of the type mentioned above that the guide paths are formed at portions of a guide rail which project out freely from a clamping position at the frame in the displacement directions of the slit jaws.

Due to the fact that the guide rails project out freely, this guide rail can expand without hindrance under the influence of temperature in the displacement direction.

In a preferred constructional variant of the invention, the guide paths are formed at two portions of a guide rail which project in opposite directions in a cantilevering manner from a clamping position. It is therefore possible to compensate for changes in length through unimpeded longitudinal expansion of these two portions in opposite directions.

In another constructional variant of the invention, it is provided that the guide paths are formed at two portions of the guide rail which project in one direction from a clamping position, wherein the end portion of the guide rail located opposite to the clamping position is supported in a floating manner. This guarantees compensation of changes in length of the guide rail in this direction proceeding from the clamping position. The guide rail can expand in the displacement direction, whereas changes in its position vertical to the displacement direction are impossible.

Further, in an advantageous manner, means for bending the guide rail are provided in the middle between the clamping position and the opposite end portion which is supported in a sliding manner, wherein the alignment of the two guide paths can be corrected by this bending. When the rail is bent using these means and the relative alignment of the two guide paths is adjusted, the parallelism of the slit can be influenced in this way. Accordingly, an adjustment possibility is provided which can preferably be carried out for an optimal adjustment of the slit parallelism prior to mounting the subassembly, according to the invention, in an optical device, for example, in a slit lamp.

In this connection, a particularly preferred construction consists in that a threaded pin is provided as means for bending the guide rail, wherein a bending of the guide rail in the longitudinal direction of the slit is accomplished by advancing the threaded pin. For this purpose, the guide rail, the clamping means for the guide rail, and the threaded pin should be made from the same material with the lowest possible coefficient of expansion, preferably stainless steel, so that changes in length caused by temperature influences can be compensated.

In a further construction of the invention, it is provided that slides are located across from the guide paths and are outfitted either with sliding guides or rolling body guides, the slit jaws being fastened thereto. The rolling body guides can be constructed in such a way, for example, that they engage around the guide paths.

Alternatively, it can also be provided that V-grooves which slide against the guide paths are formed at the slides. In this connection, it is advantageous when tension springs and/or pressure springs are provided for generating a pretensioning force between the slides and the guide paths, wherein one end of the spring is fixed with respect to the frame and the other end of the spring is attached to one of the slides. This ensures that the V-grooves always make contact with the associated guide paths and are thus also always aligned in the guide direction.

In one construction, tension springs are provided for this purpose and are arranged in such a way that their spring force causes the pretensioning of the V-grooves against the respective associated guide path with a first component $F_1$ and, with a second component $F_2$, causes a pretensioning of the respective slide against an actuating member which is used to adjust a distance between the slides in the displacement direction and accordingly serves for adjustment. In this way, the contact of the V-grooves against the guide path and the contact of the slide against the actuating member are ensured with a spring allocated to a slide and to a slit jaw, respectively. In addition the tension springs can be arranged in such a way that the spring force, with a third component $F_3$, prevents a rotation of the slit jaws around the displacement direction as will be shown in detail in the embodiment example.

In an advantageous manner, rolling bearings can be provided in order to minimize the friction between the actuating member and the slides, the displacement movement being transmitted from the actuating member to the slides via the rolling bearings. The reduced friction at this location results in a reduction in the tilting moments which are directed to the slides during the rotation of the actuating member and which accordingly involve the risk of a faulty adjustment of the slit parallelism.

It is particularly advantageous when the attachment of the tension springs to the slides is provided at least approximately in the axis of the rolling bearing arrangement, which serves to reduce the friction between the slides and the actuating member.

In order to achieve an optimum slide pairing between the V-grooves and the guide paths, the surfaces of the V-grooves and/or the surfaces of the guide paths can be provided with a friction-reducing coating, for example, a DLC layer.

The invention will be described more fully in the following with reference to two embodiment examples. Shown in the accompanying drawings are:

BRIEF DESCRIPTION OF THE DRAWINGS

In the drawings:

FIG. 1 is a schematic top view of a first constructional variant;

FIG. 2 illustrates a section AA from FIG. 1;

FIG. 3 illustrates a section BB from FIG. 2;

DESCRIPTION OF THE PREFERRED EMBODIMENTS

Figure 4:
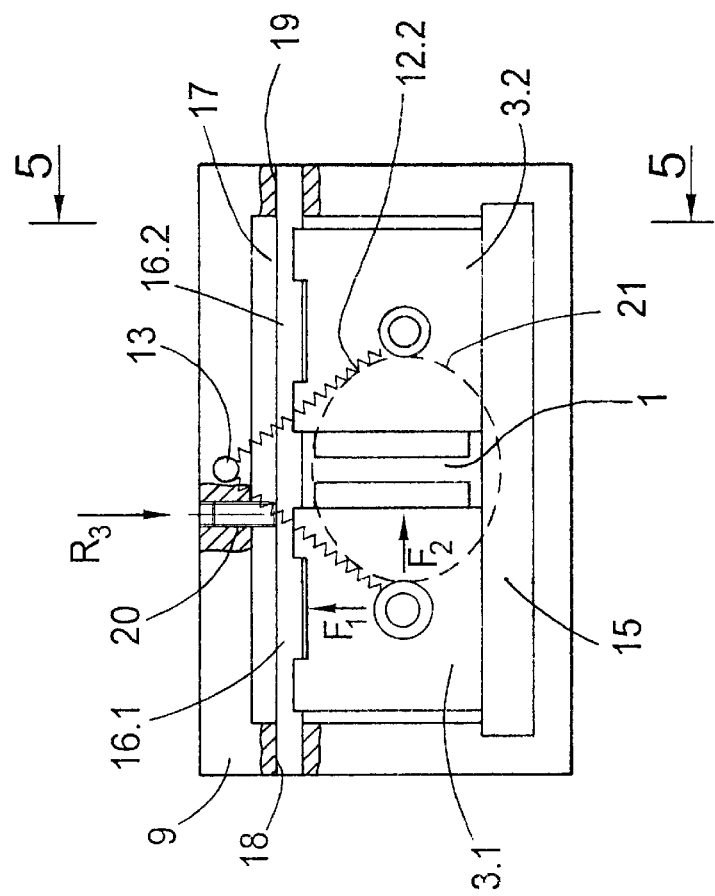
FIG. 4 is a schematic view of a second constructional variant.

FIG. 1 shows the subassembly, according to the invention, for generating an optically active slit 1 with a changeable slit width s. The slit 1 is formed between two slit jaws 2.1 and 2.2 which are arranged so as to be displaceable in directions $R_1$ and $R_2$.

The slit jaws 2.1 and 2.2 communicate, via associated slides 3.1 and 3.2, to which they are attached, with an actuating member 4 which is provided with elliptic adjusting faces 4.1 and 4.2 and which is mounted so as to be rotatable about an axis of rotation 5. The spacing between the elliptic adjusting faces 4.1 and 4.2 and the axis of rotation 5 can be changed rotating the actuating member 4 about the axis of rotation 5.

When the actuating member 4 is rotated (e.g., manually) in such a way that this spacing increases, this change in distance is transmitted to the slides 3.1 and 3.2 via the outer races, the rolling bodies and the inner races (which are fixedly connected to the slides 3.1 and 3.2) of the ball bearings 6.1 and 6.2, shown schematically, so that the slides 3.1 and 3.2 change their distance from one another and the width s of the slit 1 increases.

A precise straight-line guidance of the slides 3.1, 3.2 is required in order to ensure the parallelism of the slit jaws 2.1, 2.2. This requirement is met by a guide rail 7 which is positioned at a frame 9 in a stationary manner by means of a clamping device 8 (see FIG. 2). As can be seen in FIG. 2, two guide paths 10.1 and 10.2 of equal length are formed at the guide rail 7 and cantilever out from the clamping position in opposite directions.

Alternatively, the slides 3.1, 3.2 can be connected with the guide paths 10.1, 10.2 by sliding assemblies as well as by rolling assemblies; the invention will be explained in the following with reference to a sliding assembly corresponding to one constructional variant.

In this case, the guide paths 10.1, 10.2 have circular cross sections, while V-grooves which slide against the guide paths 10.1, 10.2 are provided at the slides 3.1, 3.2. A relatively low-friction sliding assembly is achieved when, for example, the surface of the V-grooves and/or guide paths 10.1, 10.2 are provided with a DLC layer. The groove base 11 of the V-grooves is shown in FIG. 2 in dashed lines.

FIG. 2 shows a side view of the slides 3.1, 3.2, the guide rod 7 with guide paths 10.1, 10.2, and the clamping device 8, in which the guide rod 7 is clamped in the center.

The circular cross section of the guide rail 7 can be seen in FIG. 3 (section BB from FIG. 2). This guide rail 7 is mounted in the clamping device 8 (by a sliding fit virtually without play) and can be clamped in by a clamping screw (not shown).

Tension springs 12.1 and 12.2 are provided to ensure contact of the V-grooves at the guide paths 10.1, 10.2, each tension spring 12.1 and 12.2 being attached by one of its ends to a pin 13 (see FIG. 2 and FIG. 3). The pin 13 is arranged at the frame 9 and is stationary with respect to the frame. The tension springs 12.1, 12.2 are attached by their opposite ends to pins 14 which are positioned approximately in the geometric center of the slides 3.1, 3.2. The inner races of the ball bearings 6.1, 6.2 are also arranged on the pins 14.

Therefore, each of the two tension springs 12.1, 12.2 acts with a force component $F_1$ in the direction of the guide rail 7 and accordingly brings about a secure contact of the V-groove at the associated guide path 10.1, 10.2 for each of the two slides 3.1, 3.2. Further, a spring force component $F_2$ acts in each instance in the displacement direction of the slides 3.1, 3.2, specifically, in such a way that the effective direction of the components $F_2$ is opposed to the adjusting directions $R_1$ and $R_2$ (see FIG. 1) and therefore the contact of the outer races of the ball bearings 6.1, 6.2 is secured against the elliptic adjusting surfaces 4.1, 4.2. The elliptic adjusting surfaces 4.1, 4.2 at the actuating member 4 form, in a side view, an elliptic curve 15 shown in dashed lines in FIG. 2.

When the actuating member 4 is rotated in such a way that the distances between the elliptic adjusting surfaces 4.1, 4.2 decrease toward the axis of rotation 5, the components $F_2$ act as restoring forces by means of which the slides 3.1, 3.2 are displaced opposite to directions $R_1$ and $R_2$ and the width s of the slits 1 is reduced.

The spring constant of the two tension springs 12.1, 12.2 should be selected in such a way that the force components $F_1$ are of equal magnitude in all displacement positions of the slides 3.1, 3.2. A substantial advantage of such an arrangement consists in that the spring components $F_1$ and $F_2$ act symmetric to the slit jaws 2.1, 2.2 and accordingly a tilting of the latter is ruled out.

Finally, FIG. 3 also shows that the effective forces of the tension springs 12.1, 12.2 are directed in such a way that the slides 3.1, 3.2 are acted upon by a tilting moment around the guide paths 10.1, 10.2 which is brought about by a force component $F_3$, this tilting moment being contained by a stop strip 15. This prevents rotation of the slides 3.1, 3.2 about the displacement direction.

In a construction of the invention according to FIG. 4, which differs from the previous example, guide paths 16.1 and 16.2 are provided at two portions of a guide rail 17 which is held so as to be stationary at the frame (e.g., by a press fit) at a clamping position 18 and which cantilevers in one direction from this clamping position 18 into the frame 9.

In this respect, it can be seen from FIG. 4 that the end portion of the guide rail 17 located across from the clamping point which is stationary with respect to the frame is mounted so as to be displaceable in a sliding fit 19. This arrangement ensures a change in length of the guide rail 17 caused by temperature influences because, in this case, a relative displacement takes place between the guide rail 17 and the frame 9 inside the sliding fit 19.

As in the first example, slides 3.1, 3.2 are allocated to the guide paths 16.1, 16.2. The straight-line guiding of the slides 3.1, 3.2 and the slit jaws 2.1, 2.2 at these guide paths 16.1, 16.2 is achieved in a manner analogous to the first example.

According to FIG. 4, the slit 1 is oriented at right angles to the guide rail 17. To this extent, it is easily conceivable that the parallelism of the slit 1 (assuming, of course, a high manufacturing accuracy of all parts of the subassembly) is ensured precisely when the guide paths 16.1, 16.2 are aligned with one another. In a special construction of the invention, in order to enable optimal adjustment of this alignment prior to installing the subassembly in an optical device, a threaded pin 20 is fitted into the frame 9 as an adjusting element approximately in the middle between the clamping position 18 and the sliding fit 19, wherein the advancing direction of the threaded pin 20 is represented by $R_3$. Deviations can be corrected by advancing the threaded pin 20, so that the parallelism of the slit 1 is also provided along with the adjusted alignment of the two guide paths 16.1, 16.2. Further, an automatic compensation for temperature influences is achieved when the materials for the guide rails 7, the frame 9 and the threaded pin 20 are selected for an identical and also minimized coefficient of expansion.

Further, it can be advantageously provided that the V-grooves are not formed in a continuous manner at the slides 3.1, 3.2, but rather are relief-cut between their ends so as to prevent a tilting of the slides 3.1, 3.2 in the displacement direction.

Figure 5:
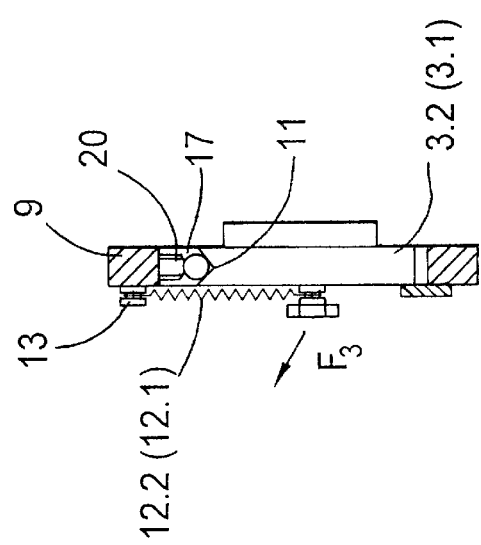
FIG. 5 illustrates a section CC from FIG. 4.

FIG. 5 shows the engagement of the threaded pin 20 on the guide rail 17 in a side view from FIG. 4.

While the foregoing description and drawings represent the preferred embodiments of the present invention, it will be obvious to those skilled in the art that various changes and modifications may be made therein without departing from the true spirit and scope of the present invention.

REFERENCE NUMBERS 1 slit
2.1, 2.2 slit jaws
3.1, 3.2 slides
4 actuating member
4.1, 4.2 elliptic adjusting faces
5 axis of rotation
6.1, 6.2 ball bearings
7 guide rail
8 clamping device
9 frame
10.1, 10.2 guide paths
11 groove base
12.1, 12.2 tension springs
13, 14 pins
15 stop strip
16.1, 16.2 guide paths
17 guide rail
18 clamping position
19 sliding fit
20 threaded pin
21 curve

What is claimed is:

1. A subassembly for generating an optically active slit with a changeable slit width s, comprising:

two slit jaws which are displaceable relative to one another at a straight-line guide and between which the slit is formed, wherein one of two guide paths is allocated to each slit jaw;

said guide paths being formed at portions of a guide rail which project out freely in the displacement directions of the slit jaws from a clamping position which is fixed with respect to the frame.

2. The subassembly according to claim 1, wherein said guide paths are formed at two portions of a guide rail which project in opposite directions in a cantilevering manner from a clamping device.

3. The subassembly according to claim 1, wherein said guide paths are formed at two portions of a guide rail which project in one direction proceeding from a clamping position, wherein the end portion of the guide rail located opposite to the clamping position is mounted in a floating manner.

4. The subassembly according to claim 3, wherein means for bending the guide rail are provided in the middle between the clamping position and the opposite end portion which is mounted in a floating manner, wherein the alignment of the two guide paths can be influenced by this bending.

5. The subassembly according to claim 4, wherein a threaded pin is provided as means for bending, wherein the threaded pin and the guide rail are made from material with the same coefficient of expansion.

6. The subassembly according to claim 1, wherein slides are located across from the guide paths and are outfitted with sliding guides or rolling body guides, the slit jaws being fastened thereto.

7. The subassembly according to claim 6, wherein rolling body guides are provided at the slides and engage around the guide paths.

8. The subassembly according to claim 6, wherein V-grooves which slide against the guide paths are formed at the slides.

9. The subassembly according to claim 8, wherein tension springs and/or pressure springs are provided for generating a pretensioning force between the slides and the guide paths, wherein one end of the spring is fixed with respect to the frame and the other end of the spring is attached to one of the slides.

10. The subassembly according to claim 9, wherein tension springs are provided and are arranged in such a way that the spring force causes the pretensioning of the slides against the guide paths with a first component $F_1$ and, with a second component $F_2$, causes a pretensioning of the slides against elliptic adjusting faces formed at an actuating member, wherein the elliptic adjusting faces are provided for adjusting a spacing between the slides in the displacement direction and accordingly for adjusting the slit width s.

11. The subassembly according to claim 10, wherein the tension springs are arranged in such a way that the spring force, with a third component $F_3$, causes the pretensioning of the slides against a stop strip so that a rotation of the slit jaws around the displacement direction is prevented.

12. The subassembly according to claim 10, wherein rolling bearings are provided in order to absorb the pretensioning force and to minimize the friction between the elliptic adjusting faces and the slides.

* * * * *